(12) United States Patent
Tatout et al.

(10) Patent No.: US 8,115,054 B2
(45) Date of Patent: Feb. 14, 2012

(54) MAIZE WITH ENHANCED TOLERANCE TO FUNGAL PATHOGEN

(75) Inventors: Christophe Tatout, Salt En Dozy (FR); Bruno Grezes-Besset, Colomiers (FR); Pierre George, Levignac (FR)

(73) Assignee: Biogemma, Paris (FR)

( * ) Notice: Subject to any disclaimer, the term of this patent is extended or adjusted under 35 U.S.C. 154(b) by 173 days.

(21) Appl. No.: 12/447,023

(22) PCT Filed: Oct. 23, 2007

(86) PCT No.: PCT/EP2007/061372
§ 371 (c)(1),
(2), (4) Date: Jun. 23, 2009

(87) PCT Pub. No.: WO2008/049848
PCT Pub. Date: May 2, 2008

(65) Prior Publication Data
US 2010/0146658 A1    Jun. 10, 2010

(30) Foreign Application Priority Data
Oct. 24, 2006  (FR) ..................................... 06 09295

(51) Int. Cl.
*C12N 15/82* (2006.01)
*C12N 15/63* (2006.01)
*C12N 15/09* (2006.01)
*C07H 21/04* (2006.01)

(52) U.S. Cl. ..... 800/279; 800/285; 800/286; 435/320.1; 435/468; 536/23.1; 536/23.6; 536/24.5

(58) Field of Classification Search ........................ None
See application file for complete search history.

(56) References Cited

U.S. PATENT DOCUMENTS

| 5,728,570 | A | 3/1998 | Matern et al. | |
|---|---|---|---|---|
| 6,160,205 | A | 12/2000 | Matern et al. | |
| 6,211,432 | B1 * | 4/2001 | Boudet et al. | 800/278 |
| 7,148,406 | B2 * | 12/2006 | Helentjaris et al. | 800/298 |
| 2009/0031439 | A1 | 1/2009 | Murigneux et al. | |
| 2010/0005537 | A1 | 1/2010 | Murigneux et al. | |

FOREIGN PATENT DOCUMENTS

| EP | 0516958 A2 | 12/1992 |
|---|---|---|
| EP | 1000543 A1 | 5/2000 |
| WO | WO-93/05160 A1 | 3/1993 |
| WO | WO-97/12982 A1 | 4/1997 |
| WO | WO-99/10498 A2 | 3/1999 |
| WO | WO-99/24561 A2 | 5/1999 |
| WO | WO-01/34817 A2 | 5/2001 |
| WO | WO-2006/010646 A1 | 2/2006 |
| WO | WO-2006/035045 A1 | 4/2006 |

OTHER PUBLICATIONS

Anterola et al., Trends in lignin modification: a comprehensive analysis of the effects of genetic manipulations/mutations on lignification and vascular integrity, Phytochemistry, vol. 61, 2002, pp. 221-294.
Bily et al., Dehydrodimers of Ferulic Acid in Maize Grain Pericarp and Aleurone: Resistance Factors to *Fusarium graminearum*, Phytopathology, vol. 93, No. 6, 2003, pp. 713-719.
Boudet et al., Lignin genetic engineering, Molecular Breeding, 1996, vol. 2, pp. 25-39.
Comai et al., Tilling: practical single-nucleotide mutation discovery, The Plant Journal, 2006, vol. 45, pp. 684-694.
Fofana et al., Suppression of Induced Resistance in Cucumber Through Disruption of the Flavonoid Pathway, Phytopathology, vol. 95, No. 1, 2005, pp. 114-123.
Goujon et al., Down-regulation of the AtCCR1 gene in *Arabidopsis thaliana*: effects on phenotype, lignins and cell wall degradability, Planta, 2003, vol. 217, pp. 218-228.
Lamb et al., Emerging Strategies for Enhancing Crop Resistance to Microbial Pathogens, Biotechnology, vol, 10, Nov. 1992, pp. 1436-1445.
Pichon et al., Cloning and characterization of two maize cDNAs encoding Cinnamoyl-CoA Reductase (CCR) and differential expression of the corresponding genes, Plant Molecular Biology, vol. 38, pp. 671-676, 1998.
U.S. Appl. No. 11/664,171, 2007.
U.S. Appl. No. 12/447,086, 2009.
U.S. Appl. No. 12/743,921, 2010.

* cited by examiner

*Primary Examiner* — Brent T Page
(74) *Attorney, Agent, or Firm* — Connolly Bove Lodge & Hutz LLP

(57) ABSTRACT

The present invention relates to the field of the improvement of the tolerance of maize to fungal pathogens and in particular to fusariosis by the qualitative and/or quantitative modification of the lignin biosynthesis pathway.

8 Claims, No Drawings

MAIZE WITH ENHANCED TOLERANCE TO FUNGAL PATHOGEN

RELATED APPLICATIONS

This application is a national stage application (under 35 U.S.C. §371) of PCT/EP2007/061372, filed Oct. 23, 2007, which claims benefit of French application 06/09295, filed Oct. 24, 2006.

The present invention relates to the field of maize improvement, in particular of the tolerance of maize to fungal pathogens and especially to fusariosis by the qualitative and/or quantitative modification of the lignin biosynthesis pathway.

The maizes are subject to attack by many pathogens. Among these, viruses and bacteria may be cited, but also fungal pathogens, responsible for many diseases, and sometimes for the presence of mycotoxins.

Thus, maize can be attacked by the fungi responsible for fusariosis (due to *Fusarium*, including *F. roseum*, *F. graminearum*, *F. liseola* and *F. monoliforme*), smut (common or of the inflorescences, due to *Ustilago zeae* or *Ustilago maydis*), anthrachnosis (*Colletotrichum graminicoia*), kabatiellosis, helminthosporosis (*Heiminthosporium turcicum*), rust (*Puccina maydis*) and mildew. In general, fungal attacks are responsible for desiccation and/or rotting of the plants, at different locations depending on the pathogen.

The fungi of the *Fusarium* genus are responsible for fusariosis, and the species *F. graminearum* and *F. monoiiforme*, which are pathogenic to maize and whose importance varies depending on the climatic conditions and the precocity of the maize varieties, may be cited. Fusariosis of the cob can be distinguished from fusariosis of the stem, the infection processes being very different. However, certain pathogenic agents are common to the two types of fusariosis. Several modes of contamination of the plant by the fungus are known, such as the penetration of the infectious mycelium into the plant via lesions attributable to insects or birds, or direct penetration at the level of the cob silk leading to infection of the grains. In the case of fusariosis of the stem, the contamination can also take place via the seeds or more rarely the roots.

Fusariosis of the cob which results in the destruction of the grains decreases the yield of the maize crops. The pathogenic agents responsible are very detrimental in other respects since they accumulate in the grains, whether or not destroyed, various mycotoxins (zearalenone, deoxynivalenol, fumonisins) which exhibit toxicity levels varying depending on the animal species and are difficult to eliminate.

Fungicidal treatments are difficult to use and only have a limited effect against the Fusaria. The best way of combating fusariosis of the cob is the use of genetic resistance. At present, few hybrids possess such resistance, and when it does exist it is partial resistance, which remains moderate.

It therefore seems important to identify methods for increasing the tolerance of maize to fungal diseases.

The approach utilized by the inventors consisted in modifying the expression of the genes of the phenyl-propanoid pathway, and more particularly the lignin biosynthesis pathway. This phenylpropanoid pathway, starting from phenylalanine, leads to the synthesis of a great variety of substances such as the anthocyanins, isoflavonoids, stilbenes, esters of hydroxycinnamic acids, or indeed to lignin. Lignin imparts rigidity to the cell walls and impermeability to the vascular tissues. Thus, modifications in the phenylpropanoid pathway have consequences for the synthesis of lignin.

A link between lignin and tolerance to pathogens is commonly suggested, lignin having in particular a role as a physical barrier against external pathogens, limiting the penetration of the pathogens. Thus, during incompatibility reactions there is accumulation of lignin at the site of the HR (hypersensitive response).

However, no direct demonstration of this role has been described in the prior art.

However, many teams have worked on the inhibition of enzymes of the lignin biosynthesis pathway in order to modify the quantity or the quality of maize lignins, in particular to obtain plants exhibiting increased digestibility.

The modification of the lignins content and composition of the plants can be achieved by overexpressing or underexpressing one or more genes of the lignins biosynthesis pathway (Anterola and Lewis, 2002, Phytochemistry, 61, 221-294). Such studies have been described in particular in the patent applications WO9924561, EP0516958, WO9305160 and WO9712982 which disclose the various strategies devised.

Cinnamoyl coenzyme A reductase (CCR) is involved in the lignins' biosynthesis pathway to convert p-coumaroyl CoA, feruloyl CoA and sinapoyl CoA into aldehydes. The existence of these three substrates suggests that either there are several isoforms of CCR or that the CCR or CCRs are capable of catalyzing reactions starting from a great variety of substrates, unless there are different isoforms of CCR depending on the cell type. At present, none of these hypotheses has been clearly proven.

In maize, at present, two isoforms of CCR have been isolated (Pichon et al., 1998, Plant Mol Biol, 38, 671-676). It would seem that only CCR1 (SEQ ID No.1) is involved in the lignins' biosynthesis pathway.

Caffeoyl coenzyme A O-methyl transferase (CCoAOMT) is an important enzyme in the biosynthesis pathway of the monolignols and more particularly of the G subunits. CCoAOMT seems to be involved in the course of several stages in the lignins' biosynthesis pathway. Thus it could be involved in an alternative methylation pathway in the biosynthesis of lignins in the zinnia, and the methylation pathway mediated by CCoAOMT would probably be one of the general pathways for the biosynthesis of lignins during the growth and development of the plant.

In maize, two genes code for CCoAOMT, the gene CCoAOMT1 and the gene CCoAOMT2, The gene CCoAOMT2 is located on chromosome 9, the gene CCoAOMT1 being located on chromosome 6.

The patent applications WO9910498 and WO0134817 relate inter alfa to the CCoAOMT1 gene of maize.

Cinnamate 4-hydroxylase (C4H) exists in two forms at least, depending on the species under consideration (C4H-1 and C4H-2). The C4H-1 form is involved in lignification and the metabolism of the phenyl-propanoids, while the role of the C4H-2 form is not yet very clear. Experiments on the deregulation of C4H-1 suggest that this gene is a limiting step in the formation of lignins, the deregulation apparently resulting in a progressive diminution and a quantitative reduction (S/G ratio) in the lignin.

4-coumarate:CoA ligase (4CL) is generally present in the form of a multigene family the isoforms whereof have different substrate specificities, and likewise different spatial/temporal expression profiles. Its role in lignification has in particular been studied in tobacco and in *Arabidopsis*.

Bily et al., 2003 (Phytopathology 93: 712-719) worked on the relationship between the wall compounds and the resistance of maize to *Fusaria* in different varieties of maize. They observed the presence of a greater quantity of dimers of ferulic acid in the varieties exhibiting greater resistance to the *Fusaria*, and in contrast no correlation has been demonstrated between the resistant varieties and the presence of monomers of ferulic acid or p-coumaric acid. These studies highlight the importance of components associated with lignin in tolerance towards pathogens, but do not make it possible to make any hypothesis as to a possible manipulation of the lignin biosynthesis pathway to increase the tolerance to fungal pathogens.

Thus, while it is well known that the autologous genes involved in the lignin biosynthesis pathway can be manipulated to modify the quality and/or quantity of lignin, it has not been demonstrated that such manipulation could increase tolerance to fungal pathogens.

The present invention provides unexpected experimental results, demonstrating that the deregulation (inhibition) of enzymes in the lignin biosynthesis pathway in maize increases the tolerance of said maize to fungal pathogens.

DESCRIPTION

The present invention thus relates to a method for increasing tolerance to a pathological fungus in maize comprising a step consisting in qualitatively and/or quantitatively altering the synthesis of lignin by the total or partial inhibition of the expression of at least one gene involved in the biosynthesis pathway for lignin (or the phenylpropanoids), the tolerance to said fungal pathogen being increased relative to maize wherein said gene is not inhibited and/or the synthesis of lignin has not been altered. The tolerance or resistance to fungal diseases according to the invention is understood to be a delay in the appearance of symptoms after infection by the pathogen for the plant according to the invention relative to a control plant and/or a lower intensity of the symptoms observed at a given date after infection (in particular the attacked surface of the leaves).

"Quantitative modification of the synthesis of lignin" is understood to mean a decrease in the quantity of lignin in the modified maize according to the invention relative to a normal maize (control not modified according to the invention), evaluated for example by measurement of the Klason lignin or of the lignin obtained by acid detergent (acid detergent lignin) by methods well known in the art (see for example Jung et al., J Agric Food Chem., 1999 May; 47(5): 2005-8, Jung et al., J Dairy Sci. 1997 August; 80(8): 1622-8).

"Qualitative modification of the synthesis of lignin" is understood to mean modification of the composition of the lignin of the modified plant relative to a control plant (not modified according to the invention), for example a change in the ratio of the S/G subunits or a change in the quality of ferulic acid. The methods for qualitative analysis of lignin are likewise known in the art. NMR can in particular be cited.

In a particular embodiment of the invention, the gene in the lignin biosynthesis pathway is selected from the genes coding for the enzymes: cinnamoyl CoA reductase 1 (CCR1, EC 1.2.1.44, SEQ ID No.1 and SEQ ID No.2), caffeoyl coenzyme A 3-O-methyl transferase (CCaOMT, SEQ ID No.3 and SEQ ID No.4), cinnamate 4-hydroxylase (C4H, SEQ ID No.5) and 4-coumarate:CoA ligase (4CL, SEQ ID No.6). It should be noted that the sequences provided in the list of sequences must only be regarded as illustrations of these alleles. It is clear that the person skilled in the art, utilizing these sequences, is capable of isolating these same genes for other varieties of maize (other alleles), in particular by isolating, in the genome of another variety, the allele in question by PCR or Southern Blot, and then sequencing it.

In a preferred embodiment, the gene for the lignin biosynthesis pathway the expression whereof is inhibited is the CCR1 gene, for which the sequences of representative alleles of maize are SEQ ID No.1 and SEQ ID No.2.

Thus, the invention is preferably implemented by totally or partially inhibiting the CCR1 gene represented by SEQ ID No.1 (or any other allele) in maize.

The inhibition of a gene involved in the lignin biosynthesis pathway can be achieved by any means known in the art. Thus, the mutation of the genes can be effected by insertion of a transposable element or of a transfer DNA (T-DNA). Physical or chemical mutagenesis can also be effected, in particular by the use of EMS, X-rays or ultraviolet.

The plants thus mutated are screened for example by PCR, utilizing primers situated in the target gene. However, it is also possible to utilize other screening methods, such as Southern Blots or screening via the AIMS method described in WO 99/27085 (for detecting insertions), by utilizing probes specific for the target genes, or methods for detecting point mutations or small insertions/deletions utilizing particular endonucleases (Cel I, Endo I) such as are described in WO 2006/010646.

In another embodiment, the inhibition is achieved by transformation of the plant with a vector containing a sense or antisense construct of the target gene. These two methods are known for enabling the inhibition of the target gene. The RNA interference method (RNAi), which is particularly effective for the silencing of genes in plants, is also utilized. This method is well known to the person skilled in the art and consists in the transformation of the plant with a construct producing, after transcription, a double-strand duplex of RNA, one of the strands whereof is complementary to the mRNA of the target gene.

The invention also makes it possible to obtain a maize exhibiting tolerance to a fungal pathogen, in particular of the *Fusarium* genus, preferably selected from *F. graminearum, F. liseola, F. roseum* and *F. monoliforme*. The maize also exhibits tolerance to the other fungal pathogens cited above and in particular to the pathogens of the *Helminthosporium* genus, in particular *H. turcicum*.

In a preferred embodiment, the present invention is implemented by utilizing a favorable allele of the CCR1 (called Δ 3318) of maize, an insertion having been effected into the first intron of the gene coding for that enzyme. The sequence of the corresponding mRNA of the maize CCR1 is available under the Genbank number X89083 (SEQ ID No.5), with a coding part of the nucleotides 79 to 1194. It is clear that these sequences are only given as examples, and that the person skilled in the art is able himself to identify the genomic and/or mRNA sequences of the CCR1 for different varieties of maize. Thus, another allele corresponding to the CCR1 of non-mutated maize is represented by the access number Y13734 (GenBank).

Maize grains having the allele Δ 3318 were deposited at NCIMB Limited, 23 St Machar Drive, Aberdeen, Scotland, AB24 3RY, UK, on 23 Jul. 2004, under the provisions of the Treaty of Budapest, under the number NCIMB 41236. This maize containing the allele Δ3318 was described in WO 2006/035045, the teaching whereof is included by reference.

In the preferred embodiment of the invention, for maize, this relates to a method for obtaining a maize exhibiting tolerance to fungal pathogens, which comprises the step of introgression of the allele Δ3318 into said maize, said maize containing the allele Δ3318 exhibiting increased tolerance to fungal pathogens relative to a maize not containing said allele. The introgression corresponds to the progressive infiltration of the allele Δ3318 from a maize containing it into another maize not containing it, following an interspecies hybridization followed by successive return back-crossings with the recipient parent (back-cross method).

Thus, the introgression can be effected via the steps consisting in:
(a) crossing a first maize line exhibiting the allele Δ3318 with a second maize line not exhibiting said allele,
(b) genotyping the progeny obtained and selecting the progeny exhibiting the allele Δ3318, and having the best genome ratio as regards said second maize line,
(c) back-crossing said progeny with said elite second maize line utilizable for the production of hybrids,
(d) repeating steps b) and c) if necessary until an isogenic line of said second maize containing the allele Δ3318 is obtained, and
(e) optionally, effecting self-fertilization in order to obtain a plant homozygotic for the allele Δ3318.

The genotyping in step (b) is preferably effected by utilizing molecular markers (microsatellite markers for example) making it possible to define the share of each of the two parents in the progeny. Likewise, in the progeny, the maizes which have the appropriate genetic characteristic as regards the allele Δ3318 are selected in a standard manner by the methods of molecular biology (such as PCR or Southern Blot). The method and the primers described in WO 2006/035045 are preferably used.

Surprisingly, it has been shown that the repetition of the back-crossings between the lines selected in step b) and the second maize line (second maize) makes it possible to achieve the appearance of a much more pronounced phenotype in said second maize. This result is quite surprising as one would expect to observe an improvement in the tolerance to fungal diseases and in particular to fusariosis from the first crossing of the maize exhibiting the allele Δ3318 with the second maize.

The invention also relates to a method characterized in that an allele of the gene C4H, said allele being called D1938, is likewise introgressed into the maize into which the allele Δ3318 is introgressed. Grains possessing the allele D1938 were deposited at NCIMB Limited, Ferguson Building, Craibstone Estate, Bucksburn, Aberdeen, Scotland, AB21 9YA, UK, on 15 Oct. 2007, under the provisions of the Treaty of Budapest, under the number NCIMB 41507.

Preferably, the invention is implemented on "elite" plants, in other words in particular plants intended to be marketed after registration in a reference catalogue. It is important to note that the "elite" character of a plant is defined in relation to the territory envisaged for its marketing, as well as the desired agronomic feature(s). Thus, certain plants are particularly suitable for certain regions, and will thus be considered as "elite" for cultivation in those regions, whereas they will not be so for other regions, wherein for example the environmental conditions are different.

Thus, an elite plant is a plant combining the maximum of agronomic characteristics necessary for economic penetration of the targeted market. For markets for hybrids (for example the maize market), the elite nature of the plants is also evaluated in terms of their capacity for combination/production of hybrids.

Preferably, the invention is implemented with "elite" maizes. The person skilled in the art knows well the definition of an elite maize. Elite maize is understood to mean a maize intended to generate hybrids intended to be marketed by crossing with another elite maize. An elite maize is defined as such in relation to the territory envisaged for marketing and by the desired agronomic characteristic(s) for the hybrid progeny. This is in particular a maize which can be registered into a reference catalogue. Thus, depending on whether the progeny is intended for human or animal nutrition, respectively a yield of grains, or a yield per hectare and good digestibility, will be sought, when the "elite nature of the maize" is evaluated. In order to determine the elite character of a maize, hybrids obtained from this are compared with reference commercial hybrids (sold for the same purpose in the same region), by field trials, by survey and measurement of agronomic characteristics appropriate to the desired objective. A maize is defined as elite if the results obtained on the parameters studied for a hybrid obtained by crossing of said maize are greater than 90% of the results obtained for the same parameters of the reference hybrids. In the context of the present invention, in addition to the desired agronomic characteristics, the capacity for tolerance to fungal diseases, and in particular fusariosis, is studied.

Thus, an elite maize is a maize combining the maximum number of agronomic characteristics necessary for economic penetration of the targeted market. Since the maize market nowadays is a market of hybrids, the evaluation of the elite character of a maize is also effected in terms of the capacity of said maize for the combination/production of hybrids.

Thus, the present invention preferably relates to the preparation of an elite maize intended in particular for the marketing of hybrids, for human or animal nutrition or for silaging, exhibiting the allele Δ3318. This elite maize is thus homozygotic for the allele Δ3318.

In another embodiment, the invention relates to the preparation and the utilization of a hybrid maize obtained by crossing of two homozygotic parent lines, said hybrid maize exhibiting an allele Δ3318. This hybrid maize can be homozygotic (if each homozygotic parent exhibits the allele Δ3318) or heterozygotic for the allele Δ3318.

The invention also relates to a maize or a maize grain containing one or more further transgenes in addition to the allele Δ3318. Transgenes conferring male sterility, male fertility, resistance to a herbicide (in particular glyphosate, glufosinate, imidazolinone, sulfonylurea, L-phosphinotricine, triazine and benzonitrile), resistance to insects (in particular a transgene coding for a *Bacillus thuringiensis* toxin), or tolerance to water stress may be cited. These maizes can be obtained by crossing a maize containing the allele Δ3318 with a maize containing said transgene. The implementation of back-crossings followed by self-fertilization makes it possible to obtain an elite maize homozygotic for the allele Δ3318 and the transgene. However, a maize hybrid simultaneously containing the allele Δ3318 and the transgene is also included in the scope of the invention.

The invention also relates to a maize or a maize grain containing an inhibition or an underexpression of the expression of a gene of the lignin biosynthesis pathway, as well as one or more transgenes, as defined above.

EXAMPLES

These examples are presented to illustrate certain particular embodiments of the invention, and must not be regarded as restricting the field of application of the invention. In particular, other mutants, or other gene constructs, can be utilized.

Example 1

Phenotype Analysis of Mutant Maize Lines for the Genes of the Phenylpropanoid Pathway A homozygotic mutant plant and a wild homozygotic control are available for each insertion event. Given the advanced stages of introgression of the mutation, it can be considered that the mutant and the wild differ only by the presence or absence of the mutation. The experiments are performed according to the following protocol:

2 locations 3 repetitions per location artificial inoculation with *Fusarium monoliforme* scoring of the symptoms observed on cobs (score from 1 to 7). This is a visual scoring of the intensity of attack on the cobs: the attack intensity score is calculated from the percentage of the area of the cob attacked by the pathogen (Reid et al., Agriculture and Agri-Food Canada, Ottawa, Ont. Technical Bulletin 1996-5E. 40 pp). The scores correspond to: 1=0% attacked, 2=1-3%, 3=4-10%, 4=11-25%, 5=26-50%, 6=51-75% and 7=76-100%.

possibly estimation of mycotoxins (fumonisins).

In the following examples, the "locations" repetitions have been converted to "simple repetitions" in order to perform a simple statistical analysis.

The statistical analysis was performed on each mutant so as to know whether there is a difference between mutant (M) and wild or control (W).

The results demonstrate that the insertion of a transposon into the genes C4H, CCR1, 4CL2, CCoAOMT1 and CCoAOMT2, involved in the phenylpropanoids and lignin metabolic pathway to a greater or lesser extent increases the tolerance to an infection with *Fusarium monoliforme*. This effect is reproducible depending on the cultivation locations, although it may be accentuated to a greater or lesser extent depending on environmental constraints.

| Mutant B0682__C4H Method: 95.0% LSD | | | |
|---|---|---|---|
| TYPE | Number | Means | Standard Deviations |
| M | 61 | 4.42623 | 0.22603 |
| W | 70 | 4.74471 | 0.189099 |
| Contrast | Difference | ±limits | |
| M − S | −0.318485 | 0.583536 | |

* indicates a statistically significant difference

Mutant tending to be more resistant than wild

| Mutant D1938__C4H Method: 95.0% LSD | | | |
|---|---|---|---|
| TYPE | Number | Means | Standard Deviations |
| M | 72 | 2.9163 | 0.124743 |
| W | 81 | 3.8593 | 0.117351 |
| Contrast | Difference | ±limits | |
| M − S | *−0.942997 | 0.338582 | |

*statistically significant difference

Mutant more resistant than wild; environmental dependence

| Mutant A3318__CCR1 | | | |
|---|---|---|---|
| TYPE | Number | Means | Standard Deviations |
| M | 103 | 3.2961 | 0.137621 |
| W | 93 | 4.69213 | 0.143085 |
| Contrast | Difference | ±limits | |
| M − S | *−1.39603 | 0.391682 | |

*statistically significant difference

Mutant more resistant than wild; net effect of 1.4 points on average

| Mutant I1888__4CL2 | | | |
|---|---|---|---|
| TYPE | Number | Means | Standard Deviations |
| M | 95 | 4.5253 | 0.125475 |
| W | 57 | 4.5412 | 0.163631 |
| Contrast | Difference | ±limits | |
| M − S | 0.0158996 | 0.407671 | |

Mutant tending to be more resistant, but marked environmental dependence

| Mutant F0046__CCoAOMT1 | | | |
|---|---|---|---|
| TYPE | Number | Means | Standard Deviations |
| M | 98 | 2.70723 | 0.120904 |
| W | 100 | 3.04586 | 0.119426 |
| Contrast | Difference | ±limits | |
| M − S | *−0.338633 | 0.335263 | |

*statistically significant difference

Mutant more resistant than wild, moderate effect

| Mutant G2092__CCoAOMT2 | | | |
|---|---|---|---|
| TYPE | Number | Means | Standard Deviations |
| M | 81 | 3.07471 | 0.129118 |
| W | 103 | 3.71153 | 0.114828 |
| Contrast | Difference | ±limits | |
| M − S | *−0.636821 | 0.341066 | |

*statistically significant difference

Mutant more resistant than wild, moderate effect

Analysis of Mycotoxins

An estimation of mycotoxins was performed. It is observed that there is a good correlation between the level of infection and the accumulation of fumonisin. It was noticed that the level of fumonisin observed is particularly high relative to the levels observed in natural infections. The system of artificial infection into the silk channel is perhaps not the most suitable for the study of the accumulation of mycotoxins.

Example 2

Creation of Transgenic Plants Bearing an Expression Cassette Enabling the Inhibition of a Gene for Metabolism of the Phenylpropanoids a—Transformation of Maize Plants With *Agrobacterium tumefaciens* by an Antisense Construct of a Gene of the Lignin Biosynthesis Pathway: CCoAOMT.

The transformation of maize with *Agrobacterium tumefaciens* was performed by means of a vector in the form of a plasmid of about 50 kb obtained by recombination in *Agrobacterium* between a pBIOS vector and a superbinary vector (pSB1). This vector comprises in particular: a plasmid replication origin Col EI, necessary for the maintenance and the multiplication of the plasmid in *Escherichia coli*, not functional in *Agrobacterium tumefaciens*, a replication origin functional in *Agrobacterium tumefaciens*, the supplementary regions virB, virC and VirG of *Agrobacterium tumefaciens* which increase the efficiency of transformation, and genes for resistance to tetracycline (tetra) and spectinomycin (spect) under the control of promoters expressing only in bacteria.

A transfer DNA (T-DNA) bearing two expression cassettes is introduced into this vector. The first cassette comprises: the promoter sequence of CsVMV (WO 97/48819), a sequence derived from the CCoAOMT sequence of maize in antisense orientation (maize CCoAOMT1, GenBank access number AJ242980, SEQ ID No.7, nucleotides 1 to 1143) and the NOS (nopaline synthase) terminator sequence. The second cassette comprises: the rice actin gene promoter sequence and the sequence of the first intron of that gene, a gene for selection with a herbicide and an NOS terminator sequence.

The transformation was effected via the protocol of Ishida et al. (Nature Biotechnology, 14, 745-750, 1996) for transformation with *Agrobacterium tumefaciens*.

Immature cobs of a line produced under glass are taken 10 days after pollination and sterilized for 15 mins. The embryos are taken and placed in contact with a suspension of *Agrobacterium* containing the vector described above for 5 mins. After removal from the suspension of *Agrobacterium*, the embryos are cultured on a medium containing neither bacteriostatic nor selective agent. This co-culturing takes place in the dark for 4 to 7 days. After the co-culturing, the embryos are pricked out again on a fresh callogenesis medium containing the bacteriostatic and the selective agent. A callus initiates and develops from the transformed cells of these embryos. The callogenesis step takes place at 25° C. in the dark and lasts 5 weeks. The callus embryos are pricked out again on fresh medium every 2 to 3 weeks. At the end of this stage, the calluses are pricked out again on a regeneration medium for 5 weeks with repricking of the callus onto callus on fresh medium after 2 to 3 weeks. From the calluses, regeneration of plantlets is effected, and these are subjected to rooting in tubes once they are sufficiently developed. After 10-15 days in tube, the plantlets are acclimatized in a phytotron before being transferred to the greenhouse. The transformants are then cultivated and crossed with pollen from a non-transgenic plant to produce the T1 generation.

b—Transformation of Maize Plants with *Agrobacterium tumefaciens* by an RNAi Construct of a Gene of the Lignin Biosynthesis Pathway: CCoAOMT.

Construction of a vector containing a fragment of the sequence of a gene of the lignin biosynthesis pathway CCoAOMT in sense and antisense orientation.

This vector was constructed utilizing the BglII fragment of 768 by derived from the maize CCoAOMT1 sequence (access number AJ242980, SEQ ID No.7 (fragment 334-1102)) using the Gateway system (Invitrogen). This vector bears an expression cassette made up of the promoter CsVMV, the fragment from the CCoAOMT1 sequence in antisense orientation, the first intron of the rice tubulin gene, the fragment from the CCoAOMT1 sequence in sense orientation and the NOS terminator. The fragment from the CCoAOMT1 sequence was chosen to make it possible to control the expression of the CCoAOMT1 and CCoAOMT2 sequences.

This vector was utilized for the transformation of maize by biolistics as described below.

The biolistics transformation method involves the co-transformation of plant cells on the one hand with the gene of interest, and on the other hand with a plasmid bearing an expression cassette containing a selection gene (for example a herbicide-resistance gene).

Immature embryos taken 10 days after pollination are cultured on an osmotic medium for 4 days then bombarded with particles of gold coated with plasmids containing the gene of interest and the selection gene. The embryos are then pricked out again on a callogenesis medium, then the developed calluses are placed on a regeneration medium, and the plants regenerated as seen in Example 2a.

c—Phenotype Analyses of the Anti-Sense and RNAi Transformants

The protocol for artificial inoculation with *Fusarium monoliforme* described in Example 1 for mutant maize lines is utilized for testing the tolerance of the anti-sense and RNAi transformants of the CCoAOMT gene.

The methodology described in this example (sections a, b or c) for inhibiting the CCoAOMT gene can also be reproduced with other genes, and in particular the CCR1 gene.

Example 3

Genetic Association Between the CCR1 Gene, CCoAOMT1, CCoAOMT2, C4H and Tolerance to Fusariosis in Maize In order to compare the potential effect of the various alleles of the CCR1 gene in maize, association studies are performed.

These association studies, also termed linkage disequilibrium analysis, make it possible to associate a given allele with a particular phenotype. The term "linkage disequilibrium" refers to the non-random association between two alleles taken at different loci. Thus, there is a linkage disequilibrium between two alleles (1 and 2) if the allele 1 present at a given locus has a tendency to be present in the same lines as the allele 2 at another locus. Linkage disequilibrium can be favored by several phenomena such as genetic linkage, selection, genetic drift, and the migration of mixing of populations. This method was the subject of a review as regards plants (Flint-Garcia et al. (2003). Rev. Plant. Biol., 54: 357-74).

Associations between a specific molecular marker of the CCR1 gene and the nature of tolerance to fusariosis are studied, taking account of the residual structuring of the panel utilized.

Specific primers of the CCR1 gene are developed. Next, the various alleles existing in the panel are identified, either by sequencing the PCR products on all of the lines, or by studying the nucleotide polymorphisms (SNPs) at one or two particular positions on all the lines. In theory, it is preferable to study as a priority the SNPs which affect the function of the protein or the expression thereof (non-synonyms or nonsense mutations) as the probability of causing the phenotype to vary is greater. However, even if the polymorphism detected does not induce a change in the amino acid sequence of the protein, it can nonetheless affect the function of the gene by altering the control of its expression, the stability, splicing or the location of the mRNA.

In statistical terms, an association is made by a variance analysis: the quantitative datum analyzed is the observed phenotype (Y) and the variable qualitative factor is the polymorphism marker (X). The variance analysis requires that the totality of the data follow a linear model of the type $Y=X\theta+e$ where e corresponds to the experimental error. The variance analysis then makes it possible to estimate the theoretical means of each factor and also the differences between these means, which determines the existence or absence of a statistical association between the polymorphism and the characteristic.

The association tests thus make it possible to determine the existence of a correlation between a nucleotide polymorphism (SNP) and resistance to fusariosis.

According the principle recalled above, with the CCR1 gene, association studies are performed on maize using a panel of about 350 lines selected to represent the genetic variability of maize but also selected for their capacity for sensitivity or tolerance to cob fusariosis. One year of experimentation was performed on this panel at two locations for one year. Each line was inoculated into the silk channel with a suspension of *Fusarium monoliforme* spore, 1-5 days after female flowering. The symptoms of sensitivity to fusariosis were scored on the spathes (score from 1-9) and on cobs at maturity (score from 1-7) for each line. The SNPs for the following genes, which are involved in the phenylpropanoids and lignin biosynthesis pathway can be identified:

C4H: cinnamic acid 4-hydroxylase (EC 1.14.13.11)

CAD: cinnamyl alcohol dehydrogenase (EC 1.1.1.195) (CAD) brown midrib protein).

PAL: inducible phenylalanine ammonia lyase fragment.

CCR: putative cinnamoyl-CoA reductase.

4C13: 4-coumarate CoA ligase 4CL3 (EC6.2.1.12).

CCoAOMT1: caffeoyl-CoA O-methyltransferase 1 (CCoAOMT-1).

CCoAOMT2: caffeoyl-CoA O-methyltransferase 2 (EC 2.1.1.104) (trans-caffeoyl-CoA 3-O-methyl-transferase 2) (CCoAOMT-2).

CCR1: cinnamoyl CoA reductase 1.

COMT: caffeic acid 3-O-methyltransferase (EC 2.1.1.68) (S-adenosyl-L-methionine:caffeic acid 3-O-methyltransferase) (COMT or CAOMT).

These SNPs can easily be identified on databases such as the TIGR (The Institute for Genomic Research) data-base or GenBank.

For each gene, a selection of SNPs (between 1-5 SNP) representing at least 95% of the allelic variability is utilized for performing the genotyping of the 350 lines in the panel. As described above, association tests are performed so as to determine the existence of a correlation between a nucleotide polymorphism (SNP) and resistance to fusariosis.

Thus, it was possible to demonstrate an association, significant at the 5% threshold, between the poly-morphism of the CCoAOMT2 gene and the variation in cob fusariosis (means adjusted at the two test locations), the gene CCoAOMT2 accounting for 8% of the phenotype variation.

These results demonstrate the involvement of the CCoAOMT2 gene in the mechanism of resistance/tolerance to fusariosis.

Example 5

Search for New Alleles for the CCR1 Gene in the Genetic Resources or in a Collection of Mutations Induced in Maize by a Chemical Agent A representative collection hereinafter referred to as "core collection" presenting maximal molecular variability with regard to both geographical and temporal criteria of origin is utilized in order to identify new alleles of the CCR1 gene by the so-called EcoTilling method described in the literature (Mejlhede et al., 2006, Plant Breeding, 125: 461-467).

Simultaneously with the screening of the "core collection", a search for "induced alleles" is performed starting from a maize collection derived from the merging of maize collections mutated with ionizing radiation or a chemical agent (EMS). This maize collection makes it possible to identify alleles not naturally present in the maize varieties existing naturally. Moreover, 5% of the mutations discovered are null alleles of CCR1 genes, in other words an allele of the CCR1 gene where the function is annulled (absence of expression). This so-called TILLING (Targeting Induced Local Lesions IN Genomes) method is described in the literature (McCallum at al. 2000, Nature Bio-technology, 18: 455-457).

The alleles derived from the Tilling or Ecotilling approaches are identified using the technology developed by Henikoff and Comal (Plant J. 2006 February; 45(4): 684-94, Annu Rev Plant Biol. 2003; 54: 375-401). For this, specific primers of the CCR1 gene are developed. The PCR product corresponding to the amplification of one copy of the CCR1 gene is next compared with an identical PCR product derived from a DNA derived from a reference variety. The mutations analysis method is performed by identification of DNA heteroduplexes created by the renaturation of DNA strands deriving from the copy of the variety tested and the reference variety. If a mutation is present in the variety tested, a pairing anomaly (or "mismatch") ensues. This anomaly is detected then cleaved by an enzyme of the endonuclease type recognizing the particular structure (for example the enzyme Cell or the enzyme EndoI). The recognition of the mismatch is then detected by electrophoresis. For example, on agarose gel, on an automatic on-plate sequencer (LICOR type) on a capillary sequencer on ABI3100 or on ABI3730.

Each difference detected constitutes a specific "haplotype" of the CCR1 gene. The importance of each haplotype is then evaluated by a phenotype evaluation.

The group of varieties exhibiting distinct haplotypes (deriving either from screening of genetic resources or from the discovery of artificially induced mutations) are crossed with a reference variety so as to have available a collection of alleles of CCR1 in a single elite genetic base.

Phenotype analyses are undertaken to determine whether the presence of a particular haplotype is correlated to resistance to fusariosis. This same type of experimentation is extended to other types of maize pathogen. A sensitivity score is then established for each variety in order to establish the correlation between the presence of a particular haplotype or mutation and a fusariosis resistance score.

Example 6

Utilization of the Identified Alleles in Varietal Selection

The haplotypes conferring the strongest resistance level are then utilized in varietal selection. Genetic mixing between the resistant variety and varieties exhibiting other agronomic qualities such as high yields, high protein levels and capacity for resistance to preharvest sprouting, makes it possible to select new varieties combining the group of desired characteristics. The allele conferring resistance to fusariosis is followed by molecular marking in the course of this process of varietal selection.

Thus the alleles identified by Tilling or EcoTilling or validated by association test make it possible to propose crossing plans between the most complementary individuals on the basis of their alleles (here one or more alleles conferring resistance to fusariosis), then to utilize the knowledge accumulated for proposing pertinent crossings of potential parents in order to pyramid genes (accumulate various haplotypes) that should lead to the obtention of improved varieties.

The invention claimed is:

1. A method for increasing tolerance to a fungal pathogen in maize comprising qualitatively or quantitatively altering the synthesis of lignins, by total or partial inhibition of the expression of a gene coding for cinnamoyl CoA reductase (CCR) in a maize plant, and cultivating said maize plant in the presence of a fungal pathogen, the tolerance to said fungal pathogen being increased in said maize plant relative to a non-altered maize plant.

2. The method of claim 1, wherein the fungal pathogen is of the *Fusarium* genus.

3. The method of claim 1, wherein the lignin biosynthesis pathway gene is CCR1, the sequence of a representative allele whereof is SEQ ID No.1.

4. The method of claim 1, wherein the inhibition is achieved by mutation of said gene by insertion of a transposable element or of a T-DNA or by physical mutagenesis.

5. The method of claim 1, wherein the inhibition is achieved by transformation of said maize by an antisense, or overexpression, or RNAi construct.

6. The method of claim 1, wherein said inhibition is obtained by introgression of allele Δ3318 into said maize, wherein said allele Δ3318 is present in a representative sample of seeds deposited at NCIMB under the number NCIMB 41236.

7. A method for cultivating maize plants comprising cultivating maize plants containing the Δ3318 allele in the presence of a fungal pathogen, wherein said maize plants containing the Δ3318 allele have greater tolerance to fungus than wild-type plants without the Δ3318 allele.

8. The method of claim 7, wherein said maize plants also contain the D1938 allele of the C4H gene, said D1938 allele being present in a representative sample of seeds deposited at the NCIMB under the number NCIMB 41507.

* * * * *

SEQUENCE LISTING

```
<160> NUMBER OF SEQ ID NOS: 7

<210> SEQ ID NO 1
<211> LENGTH: 1116
<212> TYPE: DNA
<213> ORGANISM: Zea mays

<400> SEQUENCE: 1
atgaccgtcg tcgacgccgt cgtctcctcc accgatgccg gcgcccctgc cgccgccgcc      60
gcaccggtac cggcggggaa cgggcagacc gtgtgcgtca ccggcgcggc cgggtacatc     120
gcctcgtggt tggtgaagct gctgctcgag aagggataca ctgtgaaggg caccgtgagg     180
aacccagatg acccgaagaa cgcgcacctc agggcgctgg acggcgccgc cgagcggctg     240
atcctctgca aggccgatct gctggactac gacgccatct gccgcgccgt gcagggctgc     300
cagggcgtct tccacaccgc ctcccccgtc accgacgacc cggagcaaat ggtggagccg     360
gcggtgcgcg gcaccgagta cgtgatcaac gcggcggcgg aggccggcac ggtgcggcgg     420
gtggtgttca cgtcgtccat cggcgccgtg accatggacc ccaagcgcgg gcccgacgtc     480
gtggtcgacg agtcgtgctg gagcgacctc gagttctgcg agaaaaccag gaactggtac     540
tgctacggca aggcggtggc ggagcaggcg gcgtgggagg cggcccggcg gcggggcgtg     600
gacctggtgg tggtgaaccc cgtgctggtg gtgggccccc tgctgcaggc gacggtgaac     660
gccagcatcg cgcacatcct caagtacctg gacggctcgg cccgcacctt cgccaacgcc     720
gtgcaggcgt acgtggacgt gcgcgacgtg gccgacgcgc acctccgcgt cttcgagagc     780
ccccgcgcgt ccggccgcca cctctgcgcc gagcgcgtcc tccaccgcga ggacgtcgtc     840
cgcatcctcg ccaagctctt ccccgagtac cccgtcccag ccaggtgctc cgacgaggtg     900
aatccgcgga agcagccgta caagttctcc aaccagaagc tccgggacct ggggctgcag     960
ttccggccgg tcagccagtc gctttacgac acggtgaaga acctccagga gaagggccac    1020
ctgccggtgc tcggagagcg gacgacgacg gaggccgccg acaaggatgc ccccgcggcc    1080
gagatgcagc agggagggat cgccatccgt gcctga                              1116

<210> SEQ ID NO 2
<211> LENGTH: 1116
<212> TYPE: DNA
<213> ORGANISM: Zea mays

<400> SEQUENCE: 2
atgaccgtcg tcgacgccgt cgtctcctcc accgatgccg gcgcccctgc tgccgccgcc      60
accgcggtac cggcggggaa cgggcagacc gtgtgcgtga ccggcgcggc cgggtacatc     120
gcctcgtggt tggtgaagct gctgctcgag aagggataca ctgtgaaggg caccgtcagg     180
aacccagatg acccgaagaa cgcgcacctc aaggcgctgg acggcgccgc cgagcggctg     240
```

```
atcctctgca aggccgatct gctggactac gacgccatct gccgcgccgt gcagggctgc      300
cagggcgtct tccacaccgc ctcccccgtc accgacgacc cggagcaaat ggtggagccg      360
gcggtgcgcg gcaccgagta cgtgatcaac gcggcggcgg aggccggcac ggtgcggcgg      420
gtggtgttca cgtcgtccat cggcgccgtg accatggacc ccaagcgcgg gcccgacgtc      480
gtggtcgacg agtcgtgctg gagcgacctc gagttctgcg agaaaaccag gaactggtac      540
tgctacggca aggcggtggc ggagcacgcg gcgtgggaga cggcccggcg gcggggcgtg      600
gacctggtgg tggtgaaccc cgtgctggtg gtgggccccc tgctgcaggc gacggtgaac      660
gccagcatcg cgcacatcct caagtacctg gacggctcgg cccgcacctt cgccaacgcc      720
gtgcaggcgt acgtggacgt gcgcgacgtg gccgacgcgc acctccgcgt cttcgagagc      780 cccgcgcgt ccggccgcca cctctgcgcc gagcgcgtcc tccaccgcga ggacgtcgtc      840
cgcatcctcg ccaagctctt ccccgagtac cccgtcccag ccaggtgctc cgacgaggtg      900
aatccgcgga agcagccgta caagttctcc aaccagaagc tccgggacct ggggctgcag      960
ttccggccgg tcagccagtc gctttacgac acggtgaaga acctccagga agggacac     1020 ctgccggtgc tcggagagcg gacgacgacg gaggccgccg acaaggatgc ccccacggcc     1080
gagatgcagc agggagggat cgccatccgt gcctga                              1116
```

<210> SEQ ID NO 3
<211> LENGTH: 1197
<212> TYPE: DNA
<213> ORGANISM: Zea mays

<400> SEQUENCE: 3

```
agcagtagta atagtaggag tatattgtaa aattgaggag cattactgta ttaccgatct       60
cgtgatttac gtatcgaaac ggcggcgaca attcccaaga aggaagagga ggagaaagat      120
tacaggggca agaaagagcc aaaaaaaaag ccggtggata attaatgctg cgggtcgtct      180
attatgattg gaatgaggat gcggccggcg gcgccgtcgg tggcggtggt ggggcaggcc      240
aggccaggcc atgttttcac ttgacgcggc ggcagagggt gacgccgtcg ccgacgggga      300
gctggcagat ctcgacgcgg tcgtcggcgg cgagcgcctt gttgaggacg agcacgaagt      360
cgcggtagaa gcggatgtac ttgcgcatgg gcgcgtcgtc ggggagcacg acggagccgt      420
tccacagcgt gttgtcgtag ccgatgaggc cgcccagctt caccagcttc agcagccgct      480
cgtggtagtt gaggtagttg tccttgtcgg cgtccacgaa gacgaagtcg aacgacccgt      540
ggttcttctc ctccgcgatg aggtcgtcga ggacggggag cgcgggaccc tcgcggaagt      600
cgatcttgtg ggcgacgccg gccttctcga tgcaggcag gcccagctcg tagttctcgc      660
ggttgatgtc catggccaag atcgtgccgt cctccgggag ggcgagcgcc gtggcgagga      720
gggagtagcc ggtgtagacg ccgatctcca tggtcttctt ggcgccgatg agcttgatga      780
gcatgttcag gaactgcccc tcgtcggcgg aggtcgtcat caggttccat gggtgcttgg      840
cggtgatctc gcggagctcc ttcatgctct ccggctcccg cgggtacacg ctcgtgtcca      900
ggatgtactg gtagaggtcg tcgctcttga gcaggctctt gtggccgacc tcggagtgcc      960
gcgtcttctg ctcgccgttg ccgttggcct gctgctcctg cgccggcgcc gcctcggtcg     1020
ccgtggtggc cattgcgtgc agtgtagtta gctgaacgaa cgagtccctc ctggagatct     1080
ggggtgcggc aatagaacta gctagcgcgt cgggtactcg ggtattgctg gattgaccga     1140
ccttgcctgc cggggcggct tatataacgc gcggcggcaa ggcgcggacg cgtgggt        1197
```

<210> SEQ ID NO 4
<211> LENGTH: 1195
<212> TYPE: DNA
<213> ORGANISM: Zea mays
<220> FEATURE:
<221> NAME/KEY: misc_feature
<222> LOCATION: (1148)..(1170)
<223> OTHER INFORMATION: n is a, c, g, or t

<400> SEQUENCE: 4

| | | | | | |
|---|---|---|---|---|---|
| cgcaagccag | tgccgcgccc | agatctccgc | gacagatcag | tcgttcgtcc | agctaactgc | 60 |
| actgcacgca | atggccacca | cggcgaccga | ggcgaccaag | acgactgcac | cggcgcagga | 120 |
| gcagcaggcc | aacggcaacg | gcaacggcaa | cggcgagcag | aagacgcgcc | actccgaggt | 180 |
| cggccacaag | agcctgctca | agagcgacga | cctctaccag | tacatcctgg | acacgagcgt | 240 |
| gtaccccgcgg | gagccggaga | gcatgaagga | gctgcgcgag | atcaccgcca | agcacccatg | 300 |
| gaacctgatg | accacctccg | ccgacgaggg | ccagttcctc | aacatgctca | tcaagctcat | 360 |
| cggcgccaag | aagaccatgg | agatcggcgt | ctacaccggc | tactcgctcc | tcgccaccgc | 420 |
| gctcgcactc | ccggaggacg | gcacgatctt | ggccatggac | atcaaccgcg | agaactacga | 480 |
| gctaggcctt | ccctgcatca | acaaggccgg | cgtgggccac | aagatcgact | ccgcgaggg | 540 |
| ccccgcgctc | cccgtcctgg | acgacctcgt | ggcggacaag | gagcagcacg | ggtcgttcga | 600 |
| cttcgccttc | gtggacgccg | acaaggacaa | ctacctcagc | taccacgagc | ggctcctgaa | 660 |
| gctggtgagg | cccggcggcc | tcatcggcta | cgacaacacg | ctgtggaacg | gctccgtcgt | 720 |
| gctccccgac | gacgcgccca | tgcgcaagta | catccgcttc | taccgcgact | cgtcctcgc | 780 |
| cctcaacagc | gcgctcgccg | ccgacgaccg | cgtcgagatc | tgccagctcc | ccgtcggcga | 840 |
| cggcgtcacg | ctctgccgcc | gcgtcaagtg | aaaaaaagaa | gaagaagaaa | aaaaacataa | 900 |
| taccctgcgt | tcctgctgcc | ccggctgtct | ggcccccact | actgccaccg | acggcggcgc | 960 |
| cgcacccccg | ttccaatcat | atcgtagacg | acgcgcagca | ttaaattatc | aatcaccggc | 1020 |
| tctggctctt | tcttggccct | gtactgtact | attaatgttc | cgttcttgtt | tttttattcg | 1080 |
| gaattgtcgc | cgtttcagta | tacgtaaatc | tcgaggtcga | taatacagta | atactaccaa | 1140 |
| tttaactnnn | nnnnnnnnnn | nnnnnnnnnn | gtcgacgcgg | ccgcgaattc | ggatc | 1195 |

<210> SEQ ID NO 5
<211> LENGTH: 1719
<212> TYPE: DNA
<213> ORGANISM: Zea mays
<220> FEATURE:
<221> NAME/KEY: misc_feature
<222> LOCATION: (156)..(177)
<223> OTHER INFORMATION: n is a, c, g, or t

<400> SEQUENCE: 5

| | | | | | |
|---|---|---|---|---|---|
| acgacacaaa | cacacacccc | acctaccccg | gccggaccgg | caggcagcac | agcatggacc | 60 |
| tcgccctcct | agagaaggcc | ctgctgggcc | tgttcgccgc | ggctgtggtg | gccatcgccg | 120 |
| tggccaagct | gaccggcaag | cggtaccgcc | tcccannnnn | nnnnnnnnnn | nnnnnntgg | 180 |
| tgggaaactg | gctgcaggtg | ggcgacgacc | tgaaccaccg | caacctgatg | gccatggcga | 240 |
| agcggttcgg | cgacatcttc | ctgctgcgca | tgggcgtgcg | caacctggtg | gtggtgtcga | 300 |
| ccccggagct | ggccaaggag | gtgctccaca | cgcagggcgt | ggagttcggc | tcccgcaccc | 360 |
| gcaacgtggt | gttcgacatc | ttcacgggca | aggggcagga | catggtgttc | acggtgtacg | 420 |
| gcgaccactg | gcgcaagatg | cggcgcatca | tgaccgtccc | cttcttcacc | aacaaggtgg | 480 |
| tggcccagaa | ccgcgccggg | tgggaggagg | aggcccggct | ggtggtggag | gacgtgagga | 540 |

-continued

```
aggaccccga ggccgcggcc ggcggcgtcg tgctccgccg ccgcctccag ctgatgatgt    600
acaacgacat gttccgcatc atgttcgacc gccggttcga cagcgagcac gacccgctct    660
tcaacaagct caaggcgctc aacgcggagc gcagccgcct gtcgcagagc ttcgagtaca    720
actacggcga cttcatcccc gtgctccgcc ccttcctccg cggctacctc aaccgctgcc    780
acgacctcaa gacgcgccgc atgaaggtct tcgaggacaa cttcgtacag gagcgcaaga    840
aggtgatggc tcagactggt gagatccggt gcgccatgga tcacatcctc gaggccgaga    900
ggaagggcga gatcaaccac gacaacgtcc tctacatcgt cgagaacatc aacgtcgcag    960
cgatcgagac gacactgtgg tcgatcgagt ggggcatcgc cgagctggtg aaccacccgg   1020
ccatccagca caagctccgg gaggagctcg cctcggtgct gggcgccggc gtgcctgtga   1080
cggagccgga cctcgagcgc ctcccctacc ttcaggccat cgtcaaggag acgctccgcc   1140
tgcgcatggc catcccgctg ctggtccccc acatgaacct caacgacggc aagctcgccg   1200
gctacgacat ccccgccgag tccaagatcc tcgtcaatgc ctggttcctc gccaacgacc   1260
ccaagaggtg ggtgcggccc gacgagttcc ggcccgagcg cttcctggag gaggagaagt   1320
ccgtggaggc ccacggcaac gacttccgct tcgtgcccct tggggtcggc cgccggagct   1380
gccctgggat catcctcgcg ctgcctatca tcggcatcac cctgggccgg ctggtgcaga   1440
acttccagct gctgccgccg ccggggctgg acaagatcga caccacggag aagcccggcc   1500
agttcagcaa ccagatcgcc aagcatgcca ccatcgtctg caagcccctc gaggcctaga   1560
aatcaatgcc tgtttcctgc acgcgccccc gcagatgaag cactatgtat tttgtctttt   1620
ttttgtgtgt tgtgttttt ttactaagag gagatgtatt tcttgttcgt aaaatgcact   1680
tagtcaaatg gatcgagatt atgttgatca ttaaaccccc                        1719
```

```
<210> SEQ ID NO 6
<211> LENGTH: 2131
<212> TYPE: DNA
<213> ORGANISM: Zea mays
<220> FEATURE:
<221> NAME/KEY: misc_feature
<222> LOCATION: (31)..(41)
<223> OTHER INFORMATION: n is a, c, g, or t
<220> FEATURE:
<221> NAME/KEY: misc_feature
<222> LOCATION: (1905)..(1967)
<223> OTHER INFORMATION: n is a, c, g, or t

<400> SEQUENCE: 6
```

```
taaataggac cgggcccccc cccgagtctg nnnnnnnnnn ntatgaaaca cggtactccg     60
tagctgtatt gccgtaatca ggcttgttct ttgggtcaaa acaacatag agacgacgtc    120 tatatcgttt atgaacatta cacacagggc caacaaacag acaaactaaa acctctttct    180
ggcaacatgt gttccacagg aatacgtgtc ccttctgttg ccagttcatg aatagtagtg    240
ttaccgccat tacatcgcct ttttttttcgc agcagcgtgg tggccgtccg agaagaagct    300
gcatacgggc tcagtgaac accggcggcg agcctggctc tcaagtcctt cctcaggatc    360
ttgcccgacg ggttcttggg gatggattcg gtgaagaaga ccttgtggat cttcttgtag    420
aaaaccacct ccttggcgac gaattgcttg atctcatcct cggtgacttg agaaccttcg    480
gtccgcacga tgaaggcgac cgggatttca ccagcaaggt catcgttcat tgatacgacg    540
gcggcgtcct tgatctccgg gtgcgtgatg aggagcgcct ccagctccgc cggcggcacc    600
tggaagccct tgtacttgat gatctccttg agcctgtcga cgatgaagat ctcgtcgtcg    660
tcgtccacgt agccgatgtc tccggtgtgc agccagccgt ccttgtcgat ggtgttcttc    720
```

```
gtcgactcgg ggtcgttcag gtaacctttc atgatctgct ccccgcggat gcagatctcg      780
ccgggctggt tccggccgag ggcggcgccg gtgtcggggt cgacgatctt cagctccgcg      840
ttccgcacca cggtgccgca cgacccggac ttgacccggt acggctcctt ggcgaaggcc      900
aggcacatcg ccagcacggg gcctgcctcc gtcatcccgt accccctgccc gagcacggca     960
ttggggatct tggccatgaa ggcgtcctgg agctccttgc ccatgggcgc ggcgccggac     1020
atgaccatgc ggatggacgc gaggtcgccg gcggtcacgc gggggctctt ggcgatctcc     1080
accacgatgg gcggcacgaa gggcgcgatg gtgatcacgt acctgcgcac caggtcaacc     1140
agcgcgccca ggtcgaactt gcgcatgatc acgatggtgg agcccgcgcg caggccggcc     1200
agcagcaccg agttcagcga gtagatgtgg aacagcggca gcaggcacag caccacgtcg     1260
tccttgcgga agtacaggtt cgggttctcg ccatcaacct gctgcgcgac gctggtgatg     1320
aggctgcggt gggtgagcat gacgcccttg ggcagcccgg tggtgccgga ggagtagggc     1380
agcgcgacga cgtcgtcggg gtggatgtcg gcgtcagcct ccagctcctc ggccgcgatc     1440
agctcggcga actccacgca gccgtcgaag cgcccgtcga cggtgaccac ggggaatgcc     1500
cccgctccgc cgcgaactcc cgcaccttct tcaacggcgc aggcctcggt cacgatgagc     1560
cgggcgccgg ccgcctccgc ctggcggtgc acctcgtgcg gggtgtagaa cgggttggcc     1620
gtggtggtgg cggcgcccag gcgggcggcg cccaggaagg tgaaggcgaa ctcggggcag     1680
ttgcggagca ggctcatcac cacgtcgccc ttgcccaccc ccatggcgcg cagccccgac     1740
gcggcgcgcc gggacaggga ctccacctcc gcgtacgtgt acgacgcgcc cgtcagcccg     1800
tcgatcaggc acgcccgctc cgccacctcg cccatcttcc cgaagcagta ggtgtgcagc     1860
gccatgctgc tgtcgatctc gatgtcgggg agcttggacc ggaannnnnn nnnnnnnnnn     1920
nnnnnnnnnn nnnnnnnnnn nnnnnnnnnn nnnnnnnnnn nnnnnngtc tacggaaccc      1980
atctcagacc tttgctcgct gccggatgga ctggcttgtc ggatgtcggg caggtaacgt     2040
tgcgctgggc agctggttgg atggtagtat aggaaggaag gaaggagacg atggctggtg     2100
cggtgcgacc tcgccggggc cggacgcgtg g                                    2131
```

<210> SEQ ID NO 7
<211> LENGTH: 1136
<212> TYPE: DNA
<213> ORGANISM: Zea mays

<400> SEQUENCE: 7

```
ctcgtgcccc aacgcgctag ctagttctat tgccgcaccc cagatctcca ggagggactc       60
gttctttcag ctaactacac tgcacgcaat ggccaccacg gcgaccgagg cggcgccggc      120
gcaggagcag caggccaacg gcaacggcga gcagaagacg cggcactccg aggtcggcca      180
caagagcctg ctcaagagcg acgacctcta ccagtacatc ctggacacga gcgtgtaccc      240
gcgggagccg gagagcatga aggagctccg cgaggtcacc gccaagcacc catggaacct      300
gatgacgacc tccgccgacg agggggcagtt cctgaacatg ctcatcaagc tcatcggcgc      360
caagaagacc atggagatcg gcgtctacac cggctactcc ctcctcgcca cggcgctcgc      420
cctcccggag gacggcacga tcttggccat ggacatcaac cgcgagaact acgagctggg      480
cctgccctgc atcgagaagg ccggcgtcgc ccacaagatc gacttccgcg agggtcccgc      540
gctcccgtc ctcgacgacc tcatcgcgga ggagaagaac cacgggtcgt tcgacttcgt       600
cttcgtggac gccgacaagg acaactacct caactaccac gagcggctgc tgaagctggt      660
gaagctgggc ggcctcatcg gctacgacaa cacgctgtgg aacggctccg tcgtgctccc      720
```

```
cgacgacgcg cccatgcgca agtacatccg cttctaccgc gacttcgtgc tcgtcctcaa    780
caaggcgctc gccgccgacg accgcgtcga gatctgccag ctccccgtcg gcgacggcgt    840
caccctctgc cgccgcgtca agtgaaaaca tgccctggcc tggcctgccc caccaccgcc    900
accgacggcg ccgccggccg catcctcatt ccaatcataa tagacgaccc gcagcattaa    960
ttatccaccg gcttttttt  ttggctcttt cttgcccctg ttatctttct cctcctcttc   1020
ttcttgggaa ttgtcgctgc cgtttcgata cgtaaatcac gagatcggta atacagtaat   1080
gctcctcaat tttacaatat actcctacta ttactactgc taaaaaaaaa aaaaaa       1136
```